(12) United States Patent
Ebbett et al.

(10) Patent No.: US 8,460,251 B2
(45) Date of Patent: Jun. 11, 2013

(54) DISPENSING MEANS WITH LOCKABLE DOSE ADJUSTER AND ONE WAY VALVE

(75) Inventors: Todd Donald Ebbett, New Hamilton (NZ); Rodney Gordon Walker, Hamilton (NZ); Colin Anthony Standing, Hamilton (NZ); Robert Brian Seaman, Sydney (AU)

(73) Assignee: Novartis AG, Basel (CH)

( * ) Notice: Subject to any disclaimer, the term of this patent is extended or adjusted under 35 U.S.C. 154(b) by 725 days.

(21) Appl. No.: 12/666,532

(22) PCT Filed: Jun. 23, 2008

(86) PCT No.: PCT/EP2008/057922
§ 371 (c)(1),
(2), (4) Date: Dec. 23, 2009

(87) PCT Pub. No.: WO2009/000786
PCT Pub. Date: Dec. 31, 2008

(65) Prior Publication Data
US 2010/0174241 A1    Jul. 8, 2010

(30) Foreign Application Priority Data
Jun. 25, 2007   (NZ) ........................................ 556142

(51) Int. Cl.
*A61M 5/315*    (2006.01)
*A61M 5/00*    (2006.01)

(52) U.S. Cl.
USPC ........................................................ 604/223

(58) Field of Classification Search
USPC .................. 604/207–211, 213, 218, 223, 228
See application file for complete search history.

(56) References Cited

U.S. PATENT DOCUMENTS

| 4,142,654 A | * | 3/1979 | Doubleday et al. | 222/309 |
|---|---|---|---|---|
| 4,173,225 A | | 11/1979 | Newman | |
| 4,583,531 A | * | 4/1986 | Mattchen | 601/161 |
| 4,700,702 A | * | 10/1987 | Nilsson | 606/171 |
| 4,844,088 A | * | 7/1989 | Kambin | 600/566 |
| 5,195,663 A | * | 3/1993 | Martin et al. | 222/327 |
| 5,540,657 A | | 7/1996 | Kurjan et al. | |

(Continued)

FOREIGN PATENT DOCUMENTS

| AU | 2003236471 | 3/2004 |
|---|---|---|
| EP | 0064858 | 11/1982 |

(Continued)

OTHER PUBLICATIONS

ISR, Jun. 25, 2007.

(Continued)

*Primary Examiner* — Kevin C Sirmons
*Assistant Examiner* — Andrew Gilbert
(74) *Attorney, Agent, or Firm* — Ann R. Pokalsky, Esq.; Dilworth & Barrese, LLP

(57) ABSTRACT

An animal remedy dispensing means is described which has an elongate handle having a longitudinal axis, an inlet for receiving a remedy and an outlet aperture. The outlet has a central axis which forms an angle of between 0° and 45° with the longitudinal axis of the handle. The dispensing means includes a dosage control part which is moveable between a first position wherein the dose dispensed can be adjusted and a second position wherein the dose dispensed cannot be adjusted. A novel one way valve is also described.

24 Claims, 13 Drawing Sheets

U.S. PATENT DOCUMENTS

| | | | | |
|---|---|---|---|---|
| 5,575,799 A | * | 11/1996 | Bolanos et al. | 606/139 |
| 5,609,573 A | * | 3/1997 | Sandock | 604/22 |
| 5,951,517 A | * | 9/1999 | Lampropoulos et al. | 604/151 |
| 6,007,515 A | * | 12/1999 | Epstein et al. | 604/82 |
| 6,273,861 B1 | * | 8/2001 | Bates et al. | 600/567 |
| 6,599,272 B1 | | 7/2003 | Hjertman et al. | |
| 6,746,419 B1 | * | 6/2004 | Arnett et al. | 604/35 |
| 2002/0151855 A1 | | 10/2002 | Douglas et al. | |
| 2002/0183762 A1 | * | 12/2002 | Anderson et al. | 606/104 |
| 2003/0078496 A1 | | 4/2003 | Price et al. | |
| 2005/0085776 A1 | * | 4/2005 | Hommann et al. | 604/207 |
| 2006/0042550 A1 | | 3/2006 | Hoshiba et al. | |
| 2007/0225656 A1 | | 9/2007 | Hoyle, Jr. | |

FOREIGN PATENT DOCUMENTS

| | | |
|---|---|---|
| EP | 0109268 | 5/1984 |
| EP | 0109268 A2 | 5/1984 |
| EP | 0124359 | 11/1984 |
| EP | 0124359 A1 | 11/1984 |
| JP | 2004148106 | 5/2004 |
| WO | WO 2005/035028 A1 | 5/2005 |
| WO | WO 2005/037352 A2 | 5/2005 |
| WO | WO 2007/121854 A2 | 11/2007 |

OTHER PUBLICATIONS

Written Opinion, Mar. 25, 2009.

* cited by examiner

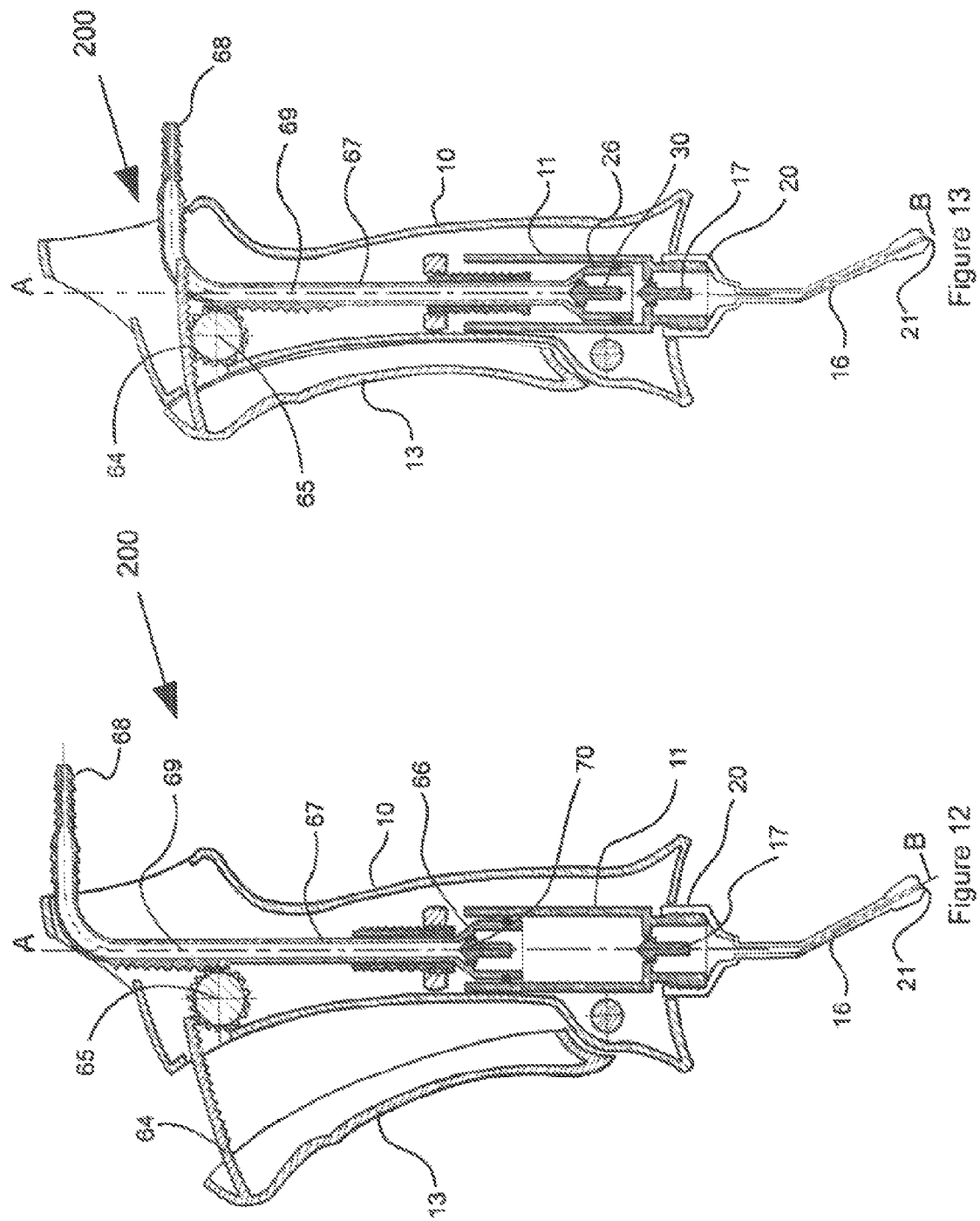

DISPENSING MEANS WITH LOCKABLE DOSE ADJUSTER AND ONE WAY VALVE

CROSS-REFERENCE TO RELATED APPLICATIONS

This application claims priority to PCT Application Number PCT/EP2008/057922, filed Jun. 23, 2008, which claims priority to New Zealand (NZ) Application Number 556142, filed Jun. 25, 2007.

The present invention relates to dispensing means, for example animal remedy dispensing means. The invention relates in particular, but not exclusively, to animal remedy dispensing means which are suitable for use in oral administration of a remedy.

BACKGROUND OF THE INVENTION

Animal remedies for sheep, cattle and the like are applied by a number of methods including topical or "pour-on" application, oral application, injection and nasal infusion. Each of these is typically dispensed from a "pistol grip" style dispensing means. One such dispensing means of the prior art is shown in FIG. 1.

As is common with applicators of the prior art the applicator has a piston or plunger 2 which can be reciprocated within a barrel 3 by squeezing and releasing a first handle 4 relative to a second handle 5. The liquid to be dispensed is drawn into the barrel 3 through an inlet 6 via a one way inlet valve 7 when the plunger 2 is withdrawn inside the barrel 3, and is dispensed through a nozzle 8 via an outlet valve 9 when the plunger 2 is extended towards the outlet valve 9.

In the dispensing means of this type the outlet nozzle 8 (or needle if the dispensing means is an injector) is substantially aligned with the central axis of the barrel 3, and the barrel 3 is orientated approximately transverse to the first handle 4. As a consequence, the outlet of the nozzle is typically substantially parallel to the forearm of the user when the dispensing means is in use, at least when the user's wrist is in a relaxed position.

When applying an animal remedy to an animal, particularly in an oral formulation, the user of the dispenser typically approaches so that he or she is facing, in substantially the same direction as the animal, if necessary the animal's read is restrained, and the dispenser is orientated so that the nozzle is inside the animal's mouth. The dispenser is then activated and a measured dose of animal remedy is dispensed into the animal's mouth. It is preferred that the outlet of the nozzle is behind the animal's tongue, to ensure that the majority of the remedy is swallowed.

The position of the user relative to the subject animal means that he or she must bend their wrist and elbow to a considerable degree in order position the nozzle in the correct position in the animal's mouth. This can be uncomfortable, and can be fatiguing if a large number of animals must be dosed.

Some dispensers of the prior art, such as the one shown in FIG. 1, have nozzles which incorporate a small bend, for example around 30°, in order to position the outlet in a more suitable orientation. While this is an improvement over straight nozzles, it does not alleviate the problem.

An additional disadvantage of the pistol grip style dispenser is that the nozzle outlet is often a considerable distance away from the user's hand. This impacts on the user's ability to determine the position of the nozzle in the animal's mouth, and also increases the force which must be used to correctly position the nozzle if the animal is resisting. This can lead to further discomfort for the user, and to injury to the animal.

As can been seen in FIG. 1, the outlet valve 9 is substantially aligned with the central axis of the barrel 3. This means that any bubbles in the fluid may become trapped in the barrel, as bubbles tend to accumulate at the top of the barrel 3 and therefore fail to pass through the outlet valve when the fluid is dispensed, if the bubbles cannot be purged from the barrel then the dose dispensed by the applicator will be incorrect.

Many animal health dispensing means of the prior art are provided with means of adjusting the dose dispensed when the applicator is used. In many applications it is critical to the health of the animal that the correct dose is applied.

One example of such a device is that described in New Zealand patent No 521084. As is common with such devices, the dose is adjusted by rotation of a dose adjustment dial, referred to as a "dosage control part" in the patent specification.

Rotation of the dose adjustment dial aligns one of a number of ribs provided on the dial with a rib on the plunger. The stroke of the plunger is limited by the length of the selected rib.

Detents are provided which tend to stop the dial at preselected angular positions which correspond to required dose volumes. However, excluding the resistance provided by the detents, the dial can be freely rotated at any time. This may lead to a user accidentally or inadvertently changing the dose, and therefore providing an animal with a suboptimal dose of remedy.

The terms "animal remedy" and "remedy" are used herein to include any preparation which may be administered to an animal and includes drugs, medicines, remedies, therapeutic preparations and the like.

The term "dose" is used herein to denote the volume of liquid dispensed by a dispensing means with a single stroke of a piston or plunger, except where the context clearly requires otherwise.

Where an angle between two axes is quantified, the angle measured is the acute angle, rather than the obtuse angle.

OBJECT OF THE INVENTION

It is an object of a preferred embodiment of the present invention to provide an animal remedy dispensing means which will overcome of ameliorate problems with dispensing means of the prior art.

It is an alternative object of a preferred embodiment to provide an animal remedy dispensing means which will provide improved comfort for a user to apply an animal health remedy to an animal.

It is a further alternative object of a preferred embodiment to minimise the chance of trauma to the animal.

It is a further alternative object of a preferred embodiment to provide a one way valve and/or a liquid dispensing means including such a one way valve which will overcome or ameliorate problems with such one way valves and/or dispensing means at present.

It is a further alternative object of a preferred embodiment to provide a dispensing means with a dosage control mechanism which will overcome or ameliorate problems with the dispensing means of the prior art.

It is a further alternative object to provide useful choice.

Other of the present invention may become apparent from the following description, which is given by way of example only.

SUMMARY OF THE INVENTION

According to one aspect of the present invention there is provided an animal remedy dispensing means including an elongate handle means having a longitudinal axis, an inlet for receiving a remedy to be dispensed, an outlet aperture separate from the inlet for dispensing the remedy, the outlet aperture having a central axis, and flow control means for controlling flow of the remedy from the inlet to the outlet, wherein the central axis of the outlet aperture and the longitudinal axis of the elongate handle means form an angle of between 0° and 45°.

Preferably the central axis of the outlet aperture and the longitudinal axis of the elongate handle means form an angle of between 0° and 35°.

Preferably the central axis of the outlet aperture is substantially parallel to the longitudinal axis of the elongate handle means.

Preferably, the position of the outlet aperture relative to the handle means is such that when the user grasps the handle means the central axis of the outlet aperture and the forearm of the user form an angle of between 30° and 90°.

Preferably the position of the outlet aperture relative to the handle means is such that when the user grasps the handle, the central axis of the outlet aperture and the forearm of the user form an angle of between 40° and 70°.

Preferably the position of the outlet aperture relative to the handle means is such that when the user grasps the handle, the central axis of the outlet aperture and the forearm of the user form an angle of substantially 60°.

Preferably the inlet is proximate a first end of the elongate handle means and the outlet aperture is proximate a second end of the handle means, opposite the first end.

Preferably the distance between the centre of the outlet aperture and the longitudinal axis of the elongate handle means is between 0 mm-38 mm.

Preferably the distance bets ee the centre of the outlet aperture and the longitudinal axis of the elongate handle means is between 10 mm-35 mm.

Preferably the flow control means includes a flow control member, and relative movement of the flow control member towards the first handle causes the remedy to flow from the outlet.

Preferably the dispensing means includes a barrel and a plunger reciprocable within the barrel upon relative movement of the first handle and the flow control member, the barrel provided with an inlet port in fluid communication with the inlet, and an outlet port in fluid communication with the outlet aperture, wherein a central axis of the barrel and the longitudinal axis of the first handle form an angle of between 60° and 90°, or more, preferably between 70° and 90°.

Preferably the central axis the barrel and the longitudinal axis of the first handle form angle of substantially 90°.

According to a second aspect of the present invention there is provided an animal remedy dispensing means including an elongate handle means, an inlet for receiving a remedy to be dispensed positioned proximate a first end of the handle, an outlet for dispensing the remedy to be dispensed positioned proximate a second end of the handle opposite the first end, and flow control means for controlling flow of the remedy from the inlet to the outlet.

Preferably the flow control means includes a flow control member, and wherein relative movement of the flow control member towards the first handle causes the remedy to flow from the outlet.

Preferably the dispensing means includes a barrel and a plunger reciprocable within the barrel upon relative movement of the first handle and the flow control member, the barrel provided with an inlet port in fluid communication with the inlet, and an outlet port in fluid communication with the outlet, and wherein a central axis of the barrel and the longitudinal axis of the first handle form an angle of between 60° and 90°, or more preferably between 70° and 90°.

Preferably the central axis of the barrel and the longitudinal axis of the first handle form an angle of substantially 90°.

Preferably the distance between the centre of the outlet aperture and a longitudinal axis of the elongate handle means is between 0 mm-38 mm.

Preferably the distance between the centre of the outlet aperture and the longitudinal axis of the elongate handle means is between 10 mm-35 mm.

According to a third aspect of the present invention there is provided an animal remedy dispensing means including handle means adapted to be grasped by a user's hand, an inlet for receiving a remedy to be dispensed, an outlet aperture separate from the inlet for dispensing the remedy to be dispensed, the outlet aperture having a central axis, and flow control means for controlling flow of the remedy from the inlet to the outlet aperture, wherein the position of the outlet aperture relative to the handle means is such that when the user grasps the handle means the central axis of the outlet aperture and the forearm of the user form an angle of between 30° and 90°.

Preferably the position of the outlet aperture relative to the handle means is such that when the user grasps the handle, the central axis of the outlet aperture and the forearm of the user form an angle of between 40° and 70°.

Preferably the position of the outlet aperture relative to the handle means is such that when the user grasps the handle, the central axis of the outlet aperture, and the forearm the user form an angle of substantially 60°.

Preferably the flow control means includes a flow control member, wherein relative movement of the flow control member towards the first handle causes the remedy to flow from the outlet.

Preferably the dispensing means includes a barrel and a plunger reciprocable within the barrel upon relative movement of the first handle, and the flow control member, the barrel provided with an inlet port in fluid communication with the inlet, and an outlet port in fluid communication with the outlet aperture, wherein a central axis of the barrel and the longitudinal axis of the first handle form an angle of between 60° and 90°, or more preferably between 70° and 90°.

Preferably the central axis of the barrel and the longitudinal axis, of the first handle form an angle of substantially 90°.

Preferably the distance between the centre of the outlet aperture and the longitudinal axis of the elongate handle means is between 0 mm-38 mm.

Preferably the distance between the centre of the outlet aperture and the longitudinal axis of the elongate handle means is between 10 mm-35 mm.

According to a fourth aspect of the present invention there is provided a liquid dispensing means, in particular an animal remedy dispensing means according to the first, second or third aspect, provided with a dosage control mechanism including a dosage control part moveable between a first position wherein the dose dispensed by the liquid dispensing means can be adjusted, and a second position wherein the dose dispensed cannot be adjusted.

Preferably the dose is adjustable by rotation of the dosage control part about an axis of rotation, and movement of the dosage control part between the first position and the second position includes a movement parallel to the direction of the axis of rotation.

Preferably the liquid dispensing means includes a housing, and the dosage control part is rotatable within the housing, wherein one of the housing and the dosage control part, is provided with at least one protruding member and the other is provided with a plurality of grooves or channels, adapted to receive at least one of the at least one protruding members when the dosage control part is in the second position.

Preferably the at least one protruding member includes a plurality of ribs.

Preferably the plurality of grooves or channels are defined by spaces between a plurality of second ribs.

Preferably activation of the dispensing means moves the dosage control part from the first position to the second position, if the dosage control part is not already in the second position when the dispensing means is activated.

According to a fifth aspect of the present invention a one way valve including a valve body having at least one aperture therethrough, a closure means adapted to allow a fluid to flow through the at least one aperture in a first direction and to substantially prevent a fluid from flowing through the at least one aperture in a second direction opposite to the first direction, wherein the valve body is provided with a flow path for receiving a fluid flowing in the second direction and directing the fluid to a required location.

Preferably the flow path extends around a periphery of the valve body.

Preferably the valve body includes a substantially cylindrical or frusto-conical portion and the flow path extends between radially opposite sides of the substantially cylindrical or frusto-conical portion.

Preferably the valve body is provided with a valve guide and the closure means includes a valve head and a valve stem slidingly engaged with the valve guide.

Preferably the closure means includes biasing means for biasing the valve head towards a sealing means.

Preferably the flow path includes a channel.

According to a sixth aspect of the present invention there is provided a liquid dispensing means, in particular an animal remedy dispensing means according to the first, second, third or fourth aspect, including a one way valve according to the fifth aspect.

Preferably the liquid dispensing means includes a barrel, aid the flow path includes a cavity defined by the channel and the barrel.

According to a seventh aspect of the present invention there is provided a liquid dispensing means including a plunger reciprocable within a barrel, the liquid dispensing means including an inlet and an outlet in fluid communication with the barrel, the liquid dispensing means further including a flow path between an area at or adjacent a top of the barrel when the liquid dispensing means is held in a normal in-use position, and the outlet.

Preferably the liquid dispensing means includes the one way valve of the fifth aspect.

According to a further aspect of the present invention there is provided an animal remedy dispensing means according to the first and/or second and/or third aspects in combination with a liquid dispensing means of the fourth aspect and/or the seventh aspect and/or a one way valve according of the fifth aspect.

The invention also broadly consists in any novel feature or combination of features disclosed herein.

BRIEF DESCRIPTION OF THE FIGURES

FIG. 12 is a cross-section side view of the dispensing means of FIG. 11, with a flow control member in a return or rest position.

FIG. 13 is a cross-section side view of the dispensing means of FIG. 12, with the flow control member in the dispensing position.

BEST MODES FOR PERFORMING THE INVENTION

Referring first to FIGS. 2 to 5 a dispensing means according to one embodiment of the present invention is generally referenced 100. In the embodiment shown the dispensing means 100 is an animal remedy dispensing means adapted for use as an oral drencher for sheep or cattle, although it may also be suitable for use with other animals such as goats.

Figure 3:
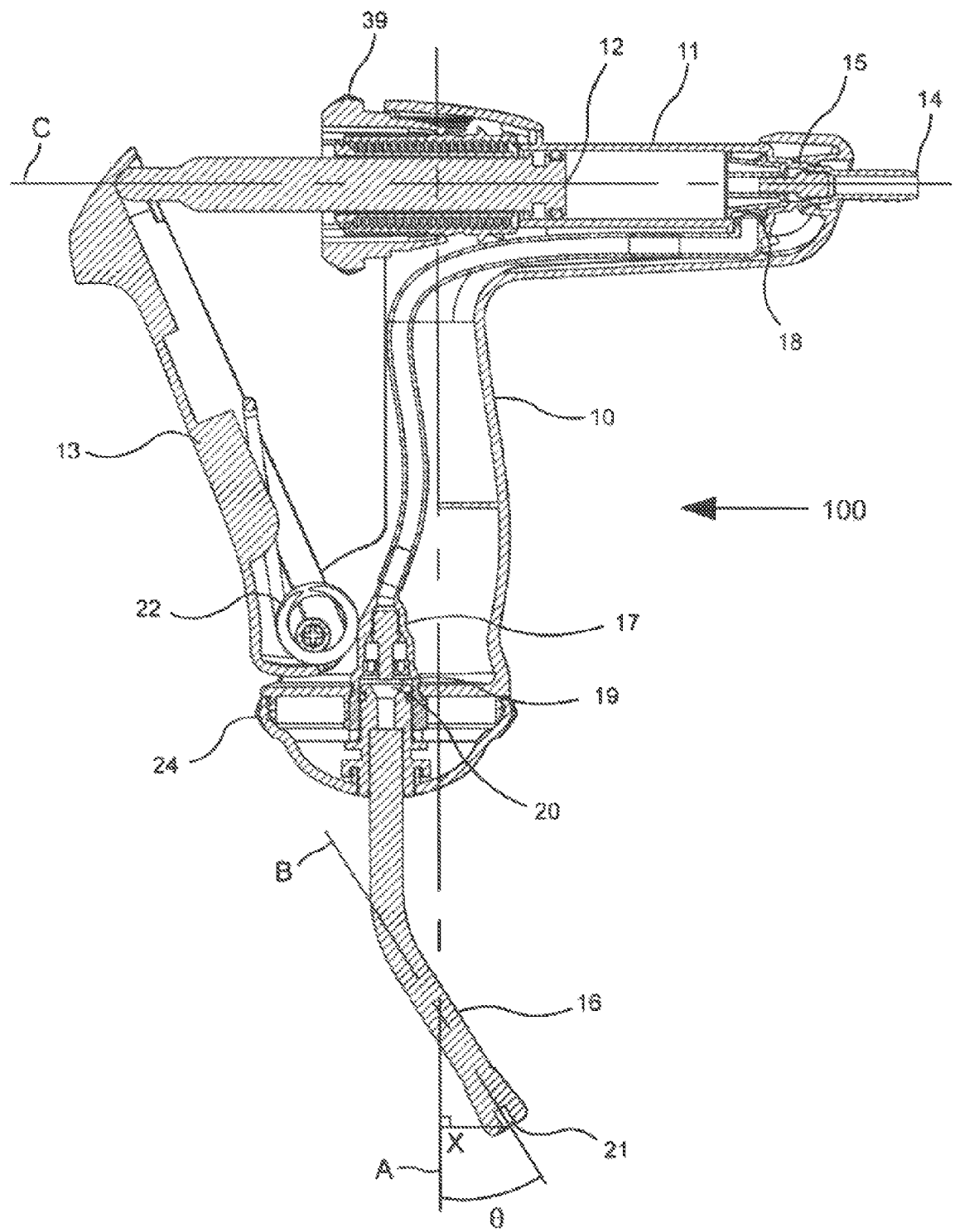
FIG. 3. Is a cross section side view of the dispensing means of FIG. 2, with the dosage control part shown in the unlocked position and the plunger withdrawn.

The dispensing means 100 includes an elongate handle means 10 having a longitudinal axis A, best seen in FIG. 3. A barrel 11 is provided at one end of the handle 10, and a piston or plunger 12 inside the barrel 11 is reciprocable under the control of flow control member, which may be a second handle 13, or a trigger or the like. The second handle 13 may actuate the plunger 12 directly, as is shown in the figures, or via a separate push rod (not shown).

The liquid to be dispensed is drawn into the barrel 11 through en inlet 14 via a one way inlet valve 1 when the plunger 12 is withdrawn inside the barrel 11, and is dispensed through a nozzle 16 via an outlet valve 17 when the plunger 1 is extended towards an outlet aperture 18 in the barrel.

Figure 5:
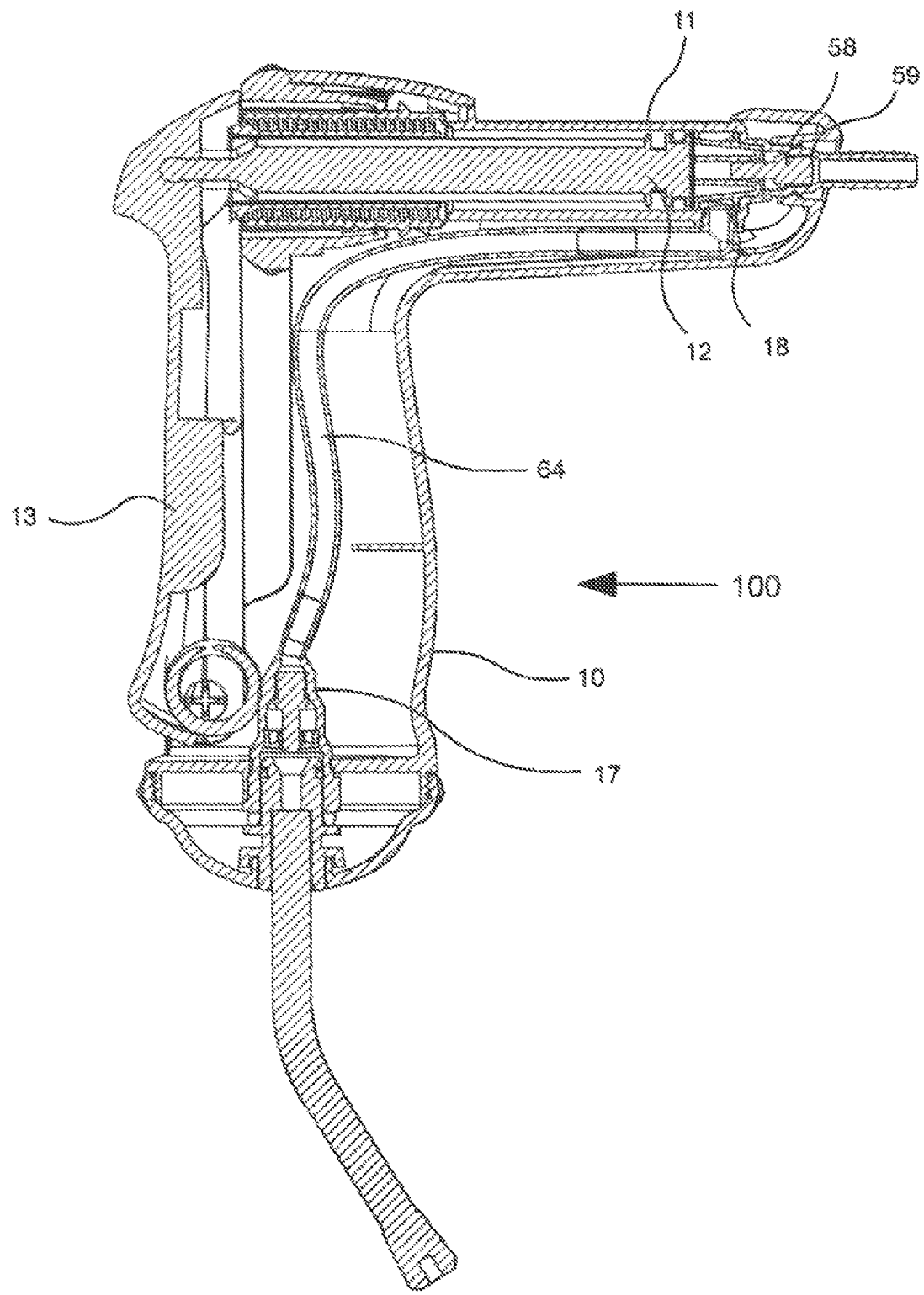
FIG. 5. Is a cross section side view of, the dispensing means of FIG. 2, with the plunger in the fully extended position and the second handle having pushed the dosage control part to, the locked position.

The "dose" dispensed by the dispensing means 100 is determined by the volume swept by the plunger 12 as it moves between a withdrawn position, as shown in FIG. 3, and the fully extended position shown in FIG. 5.

The outlet port 18 is in fluid communication with the one way outlet valve 17 which is provided at the opposite end of the elongate handle 10 from the barrel 11. The outlet valve 17 is in turn in fluid communication with an outlet aperture 19 to which an inlet aperture 20 of the nozzle 16 is connected in use. The nozzle 16 has an outlet aperture 21 at the opposite end to the nozzle inlet 20. The outlet aperture 21 has a central axis B.

Figure 4:
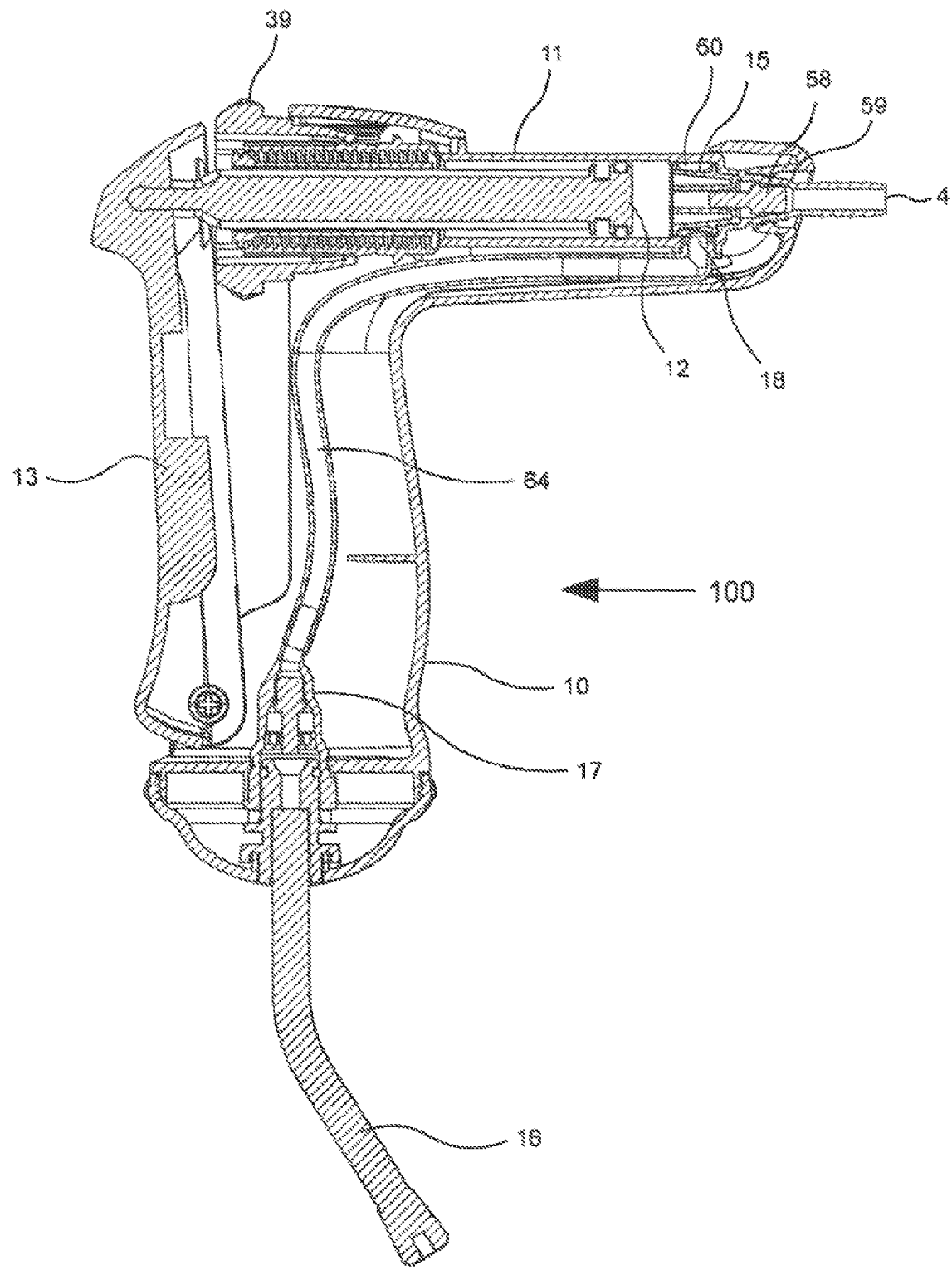
FIG. 4. Is a cross section side view of the dispensing means of FIG. 2 with the dosage control part shown in the unlocked position and the plunger almost fully extended into the barrel.

In use an animal health remedy is administered to an animal, by positioning the nozzle 16 so that the outlet aperture 21 is inside the animal's mouth and squeezing the second handle 13 towards the elongate handle 10, as shown in FIGS. 4 and 5. This causes the plunger 12 to force the preparation residing in the barrel 11 through the outlet port 18 and hence through the outlet valve 17 and the outlet aperture 21. The second handle 1 is then released and a biasing means such as a torsion spring 22 returns the second handle 13 and the plunger 12 to the rest position shown in FIGS. 2 and 3. The return movement of the plunger 1 draws a predetermined dose of the preparation from a suitable source, through the inlet 14 and into the barrel 11 through the inlet valve 15. As can be seen from FIGS. 2 to 5, in a preferred embodiment the elongate and second handles are rotatably connected at the end of the handles distal the barrel 11.

Figure 1:
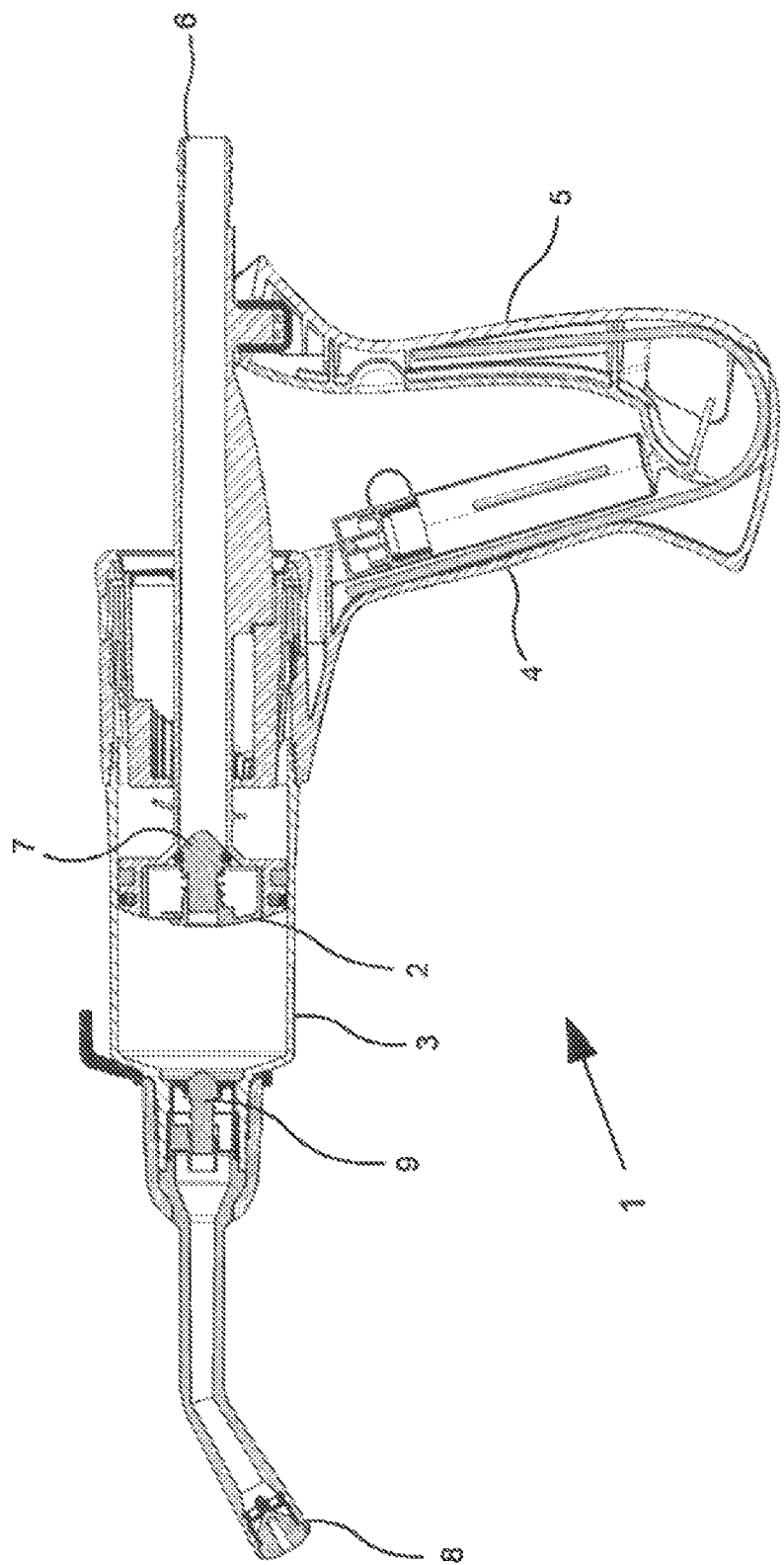
FIG. 1: Is a cross-section side view of an animal remedy dispensing means of the prior art.
Figure 2:
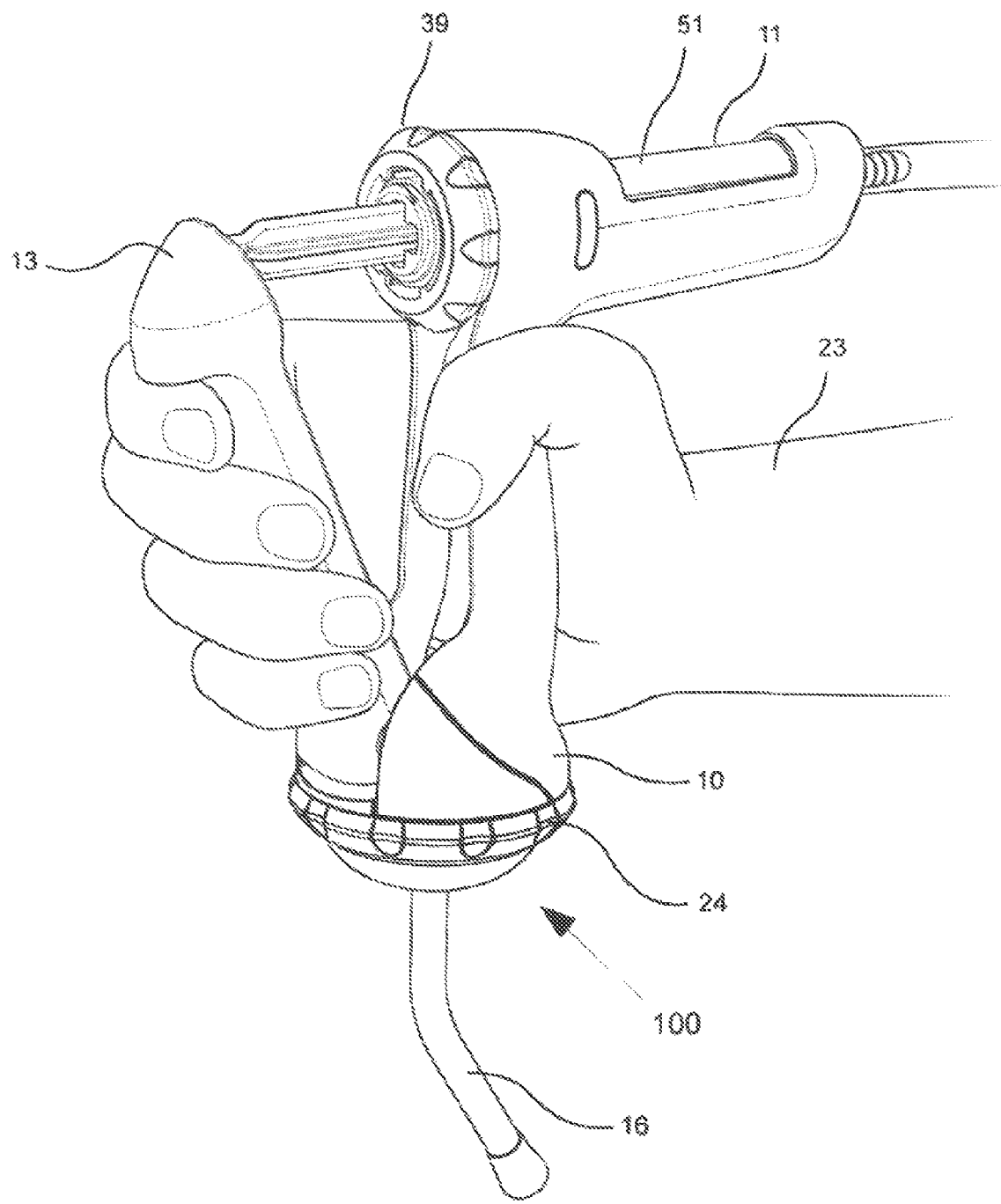
FIG. 2. Is a side perspective view of a dispensing means of the present invention, with the dosage control part in a locked position and the plunger withdrawn.

An important feature of the dispensing means 100 is that the central axis B of the outlet aperture 21 forms an angle Θ between 0 and 45°, or more preferably between 0° and 35°, with the longitudinal axis A of the elongate handle 10. In this way the angle between the central axis B of the nozzle outlet 21 and the forearm 23 of the user is between 30° and 90°, or more preferably between 40 and 70°, when the user has his or her wrist in a relaxed position, as best seen in FIG. 2. This reduces the need for the user to bend his or her wrist in order to insert the nozzle 16 into the mouth of the animal (not shown). In the most preferred embodiment the central axis B of the outlet aperture 21 forms an angle of around 32° to the longitudinal axis A, meaning that the axis B forms an angle of substantially 60° with the user's forearm.

The distance X between the longitudinal axis A of the elongate handle 10 and the centre of the outlet aperture 21 is preferably relatively small, for example between 0 mm-38 mm, or more preferably 10 mm-35 mm.

The elongate handle 10 is preferably provided with a widened base portion 24 which is dimensioned so as to be substantially incapable of entering the mouth of an animal with which the dispenser 100 is intended to be used. The widened base portion 24 forms as stop, thereby avoiding problems with the user inserting the nozzle 15 too deeply into the animal's mouth, such as may occur with the dispensers of the prior art. Although it is preferred that the elongate handle 10 be provided with a widened base portion 24, problems with determining how far to insert the nozzle into the animal's mouth may be alleviated to some extent even without the widened portion 24 in view of the extra sensitivity provided by the position of the nozzle 16 relative to the handle 10 and the user's hand 23.

Figure 6:
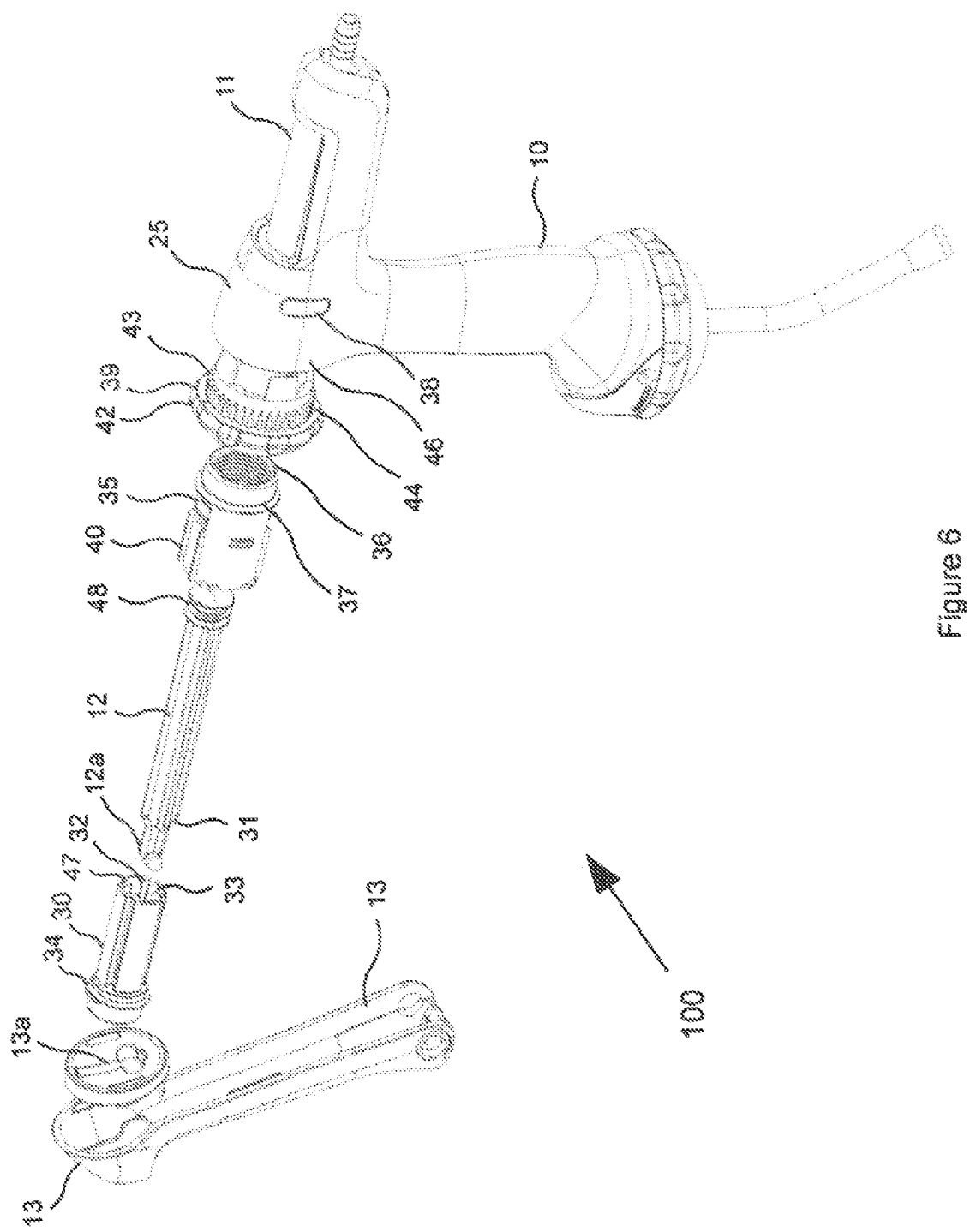
FIG. 6. Is a front perspective exploded view of the dispensing means of FIG. 2.
Figure 7:
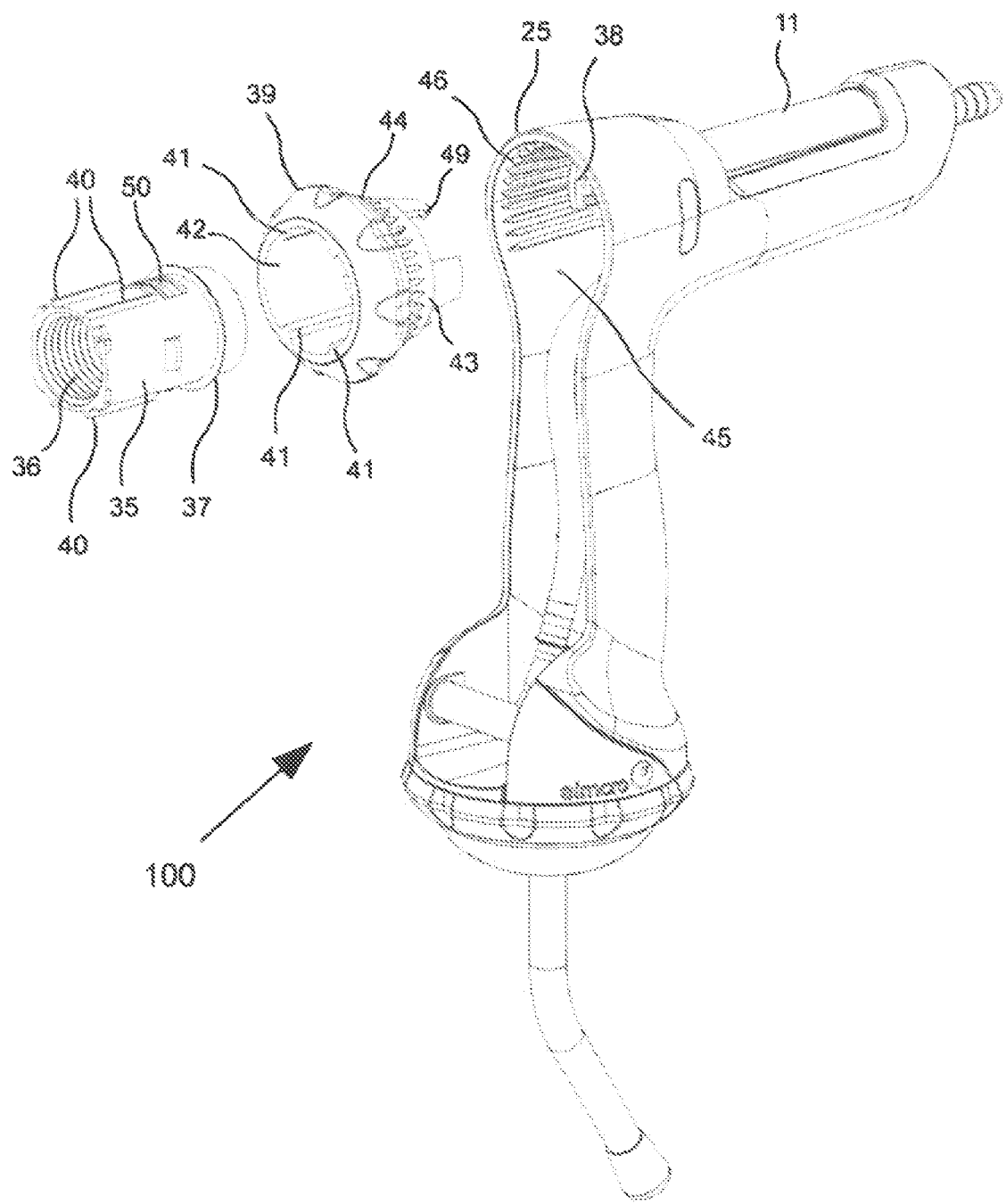
FIG. 7. Is a rear perspective exploded view of the dispensing means of FIG. 2, with the second handle, plunger and abutment member omitted for clarity.

Referring next to FIGS. 6 and 7, a preferred mechanism for varying the dose dispensed is described.

The dispensing means 100 includes a housing 25 which is connected to or integral with the elongate handle 10. The barrel 11 is connected to or formed integrally with the housing 25.

The dosage control mechanism includes an abutment member 30 which is slidably engaged with the plunger 12. The abutment member 30 is keyed to the plunger 12, for example by means of one or more ribs 31 provided on the plunger 12 which engage complimentary channels 32 provided on an internal surface 33 of the abutment member 30. The engagement of the ribs 31 with the channels 32 prevents rotation of the abutment member 30 relative to the plunger 12. The plunger is in turn prevented from moving relative to the body of the dispensing means by its connection to the second handle 13, as is described further below.

The abutment member 30 is provided with an externally threaded portion 34 along at least part of its length. A substantially cylindrical sleeve 35 is provided which fits over the abutment member 30, and which has an internal thread 36 which engages with the external threaded portion 34 of the abutment member 30. The sleeve 35 is able to rotate about the plunger 12 relative to the housing 25, but is not able to move longitudinally relative to the housing 25, in a preferred embodiment the sleeve 35 is provided with an annular rib 37 which abuts a pair of inwardly protruding tabs 38 provided inside the housing 25, one of which can be seen in FIG. 7. The tabs 38 prevent the sleeve 35 from moving outward from the housing 25, and the stepped shape of the barrel 11 and housing 25, (best seen in FIGS. 3-5) prevents the sleeve 35 from moving further inside the housing 25.

A dosage control part 39 is provided as a sliding fit over sleeve 35. The dosage control 39 part is keyed to the sleeve 35, for example by means of one or more longitudinal ribs 40 provided on an outer surface of the sleeve 35 engaging one or more inwardly protruding longitudinal ribs 41 provided inside a central aperture 42 of the dosage control part 39. The engagement of the ribs 40, 41 means that the dosage control part 39 is able to move longitudinally relative to the sleeve 35, but any rotation of the dosage control part 39 relative to the housing 25 also rotates the sleeve 35.

The outer surface 43 of the dosage control part 39 is also provided with a plurality of external ribs 44. The internal surface 45 of the housing 25 is provided with a plurality of internal ribs 46 which are spaced apart to provide a series of channels or grooves capable of receiving the externally protruding ribs 44 of the dosage control part 39.

The dosage control part 39 is slidable between a first, locked position, shown in FIGS. 2 and 5, wherein the external ribs 44 engage with the internal ribs 45 of the housing 39, and a second position, shown in FIGS. 3 and 4, wherein the external ribs 44 are clear of the internal ribs 46. When the dosage control part 39 is in the first position the interengagement of the external ribs 44 and internal ribs 46 prevents rotation of the dosage control part 39 relative to the housing 25. However the length and position of the internal and external ribs are such that when the dosage control part 39 is moved longitudinally away from the housing 25 to the second position, the external ribs 44 are clear of the internal ribs 46 of the housing 25, and the dosage control part 39 is free to rotate.

Rotation of the dosage control part 39 causes rotation of the sleeve 35. Because the threaded portion 36 of the sleeve 35 is engaged with the threaded portion 34 of the abutment member 30, the longitudinal position of the abutment member 30 changes with rotation of the sleeve 35. The inner end of the abutment member 30 has an abutment portion 47, best seen in FIG. 6, which limits the distance that an abutment portion 48 of the plunger 1 can be moved inside the barrel 11. In this way rotation of the dosage control part 39 changes the dose dispensed by the dispensing means 100.

In the embodiment shown in FIGS. 6 and 7 the plunger 12 may be removed from the barrel 11 by turning the dosage control part 39 until the threaded portion 34 of the abutment member 30 disengages from the sleeve 35. This allows maintenance of the head of the plunger 12. In some embodiments the plunger 12 may be removable by pivoting the plunger 12 so that the outer end 12a of the plunger can be disengaged from the slot 13a in the second handle 13. However, it is preferred that the plunger be retained within the slot 13a by a suitable locking means (not shown).

When engaged with the slot 13a the plunger 12 is prevented from rotating, but is able to slide within the slot relative to the second handle 13 to allow for the arcuate path followed by the end of the second handle 13 as it is squeezed towards the elongate handle 10.

In the embodiment shown the dose is adjusted by changing the distance the plunger 12 is able to withdraw within the barrel 11. The plunger 12 reaches the same position in the barrel 11 at the end of the dispensing stroke, regardless of the dose dispensed, in other embodiments not shown) the plunger may withdraw to the same position regardless of the required dose, and the dose control may be achieved by limiting the movement of the plunger away from the fully withdrawn position during the dispensing stroke.

A feature of the embodiment shown in FIGS. 2-7 is that movement of the handles 10, 13 to dispense a dose will automatically move the dosage control part from the second position, shown in FIGS. 3 and 4 to the first, locked position, shown in FIGS. 2 and 5. This means that if the dosage control member part is lift in the unlocked position, it will be moved to the locked position the next time the dispensing means is used. This may be useful in preventing inadvertent or accidental changes in the set dosage, in the embodiment shown this self locking movement is caused by one of the handles 13 abutting the end of the dosage control part 39 and pushing it towards the first position. However, in an alternative embodiment the plunger 12 may be provided with a protruding portion such as a tab or the like not shown) which performs the same function.

The dosage control part 39 is preferably provided with detent means adapted to hold it in the first position, in the embodiment shown the dosage control part 39 is provided with a plurality of inwardly facing tabs 49, best seen in FIG. 7, which releasably engage depressions or apertures 50 in the sleeve 35 when the dosage control part in the first position. A second similar detent mechanism may additionally be provided to releasably hold the dosage control part 39 in the second position.

Those skilled in the art will appreciate that although the dosage control means has been described with reference to its application to an animal health applicator, it may have application to any piston operated liquid dispensing means which dispenses a preselected, adjustable, volume of liquid. Accordingly the use of the term "dose" is not intended to limit the invention to applications in which the liquid being dispensed is an animal health remedy.

The barrel 11 is preferably transparent or at least translucent, or has a transparent or translucent portion 51, best seen in FIG. 2, so that the user is able to perform a visual check that it is filling correctly, and that there are no hubbies trapped in the barrel. Those skilled in the art will appreciate that bubbles in the barrel 11 will result in the dose of preparation dispensed being less than that required.

Referring next to FIG. 2 it can be seen that when the applicator 100 is held in its normal in use position, the barrel 11 is in a substantially horizontal orientation, although it may be tilted to one side depending on left or right handed users.

Figure 8:
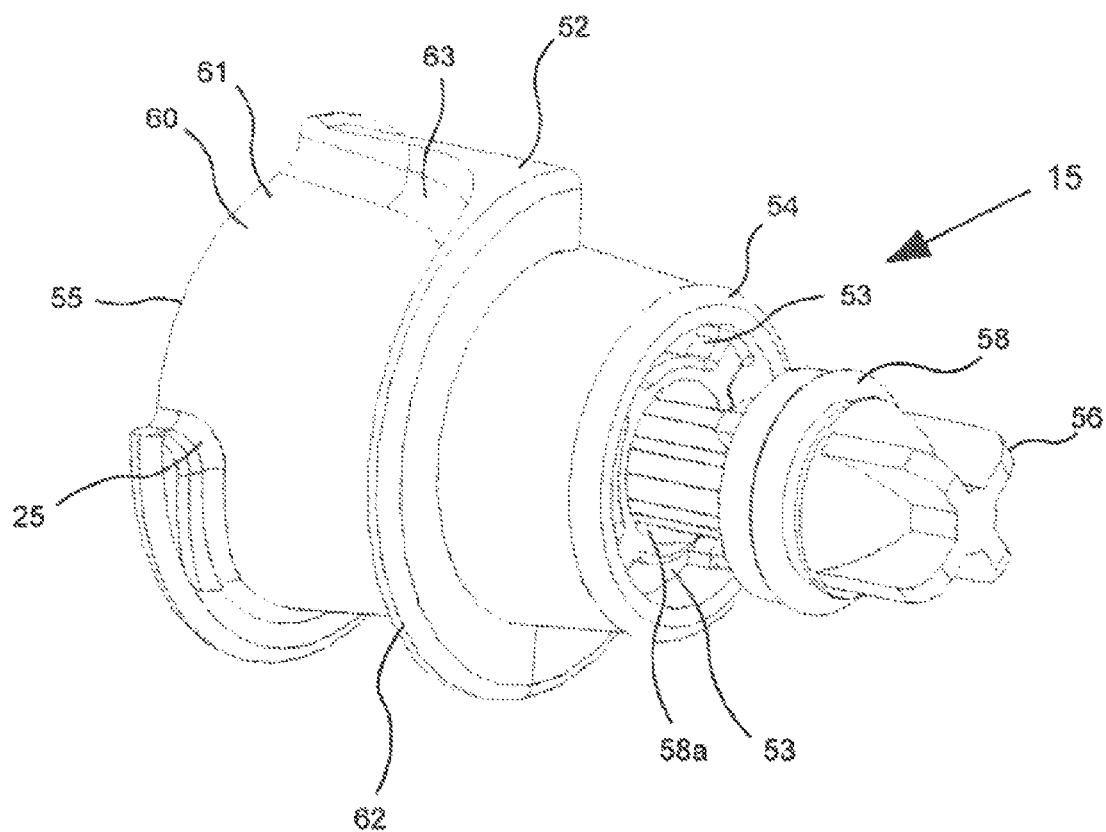
FIG. 8 Is a side perspective view of the one way inlet valve
Figure 9:
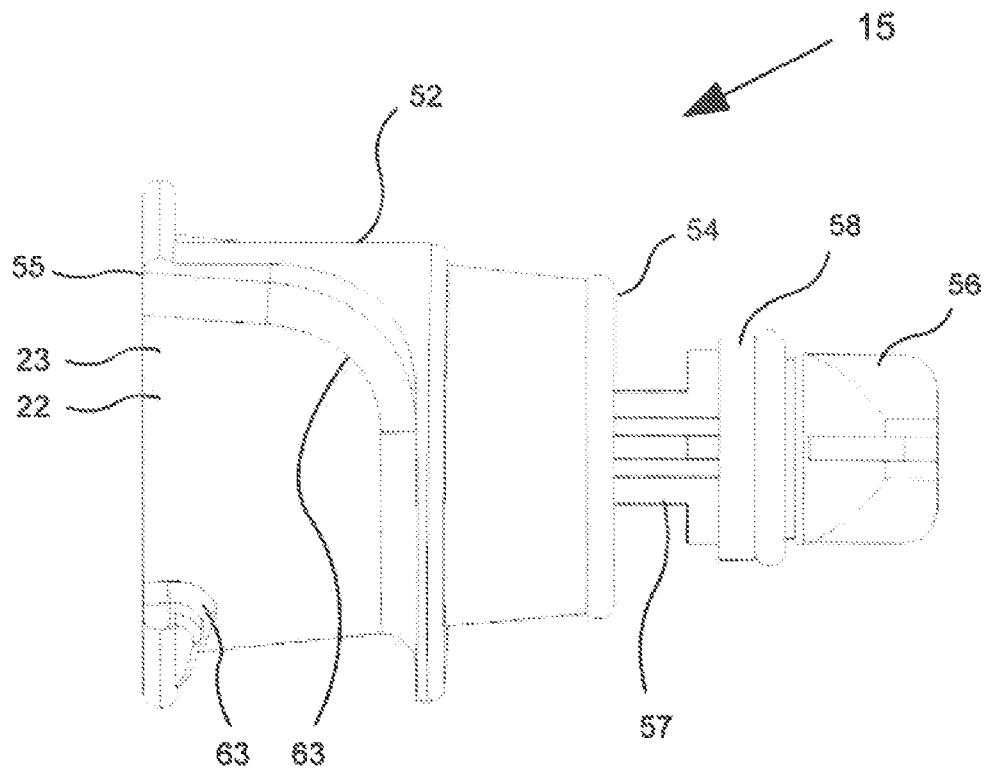
FIG. 9: Is a top view of the one way valve of FIG. 8.
Figure 10:
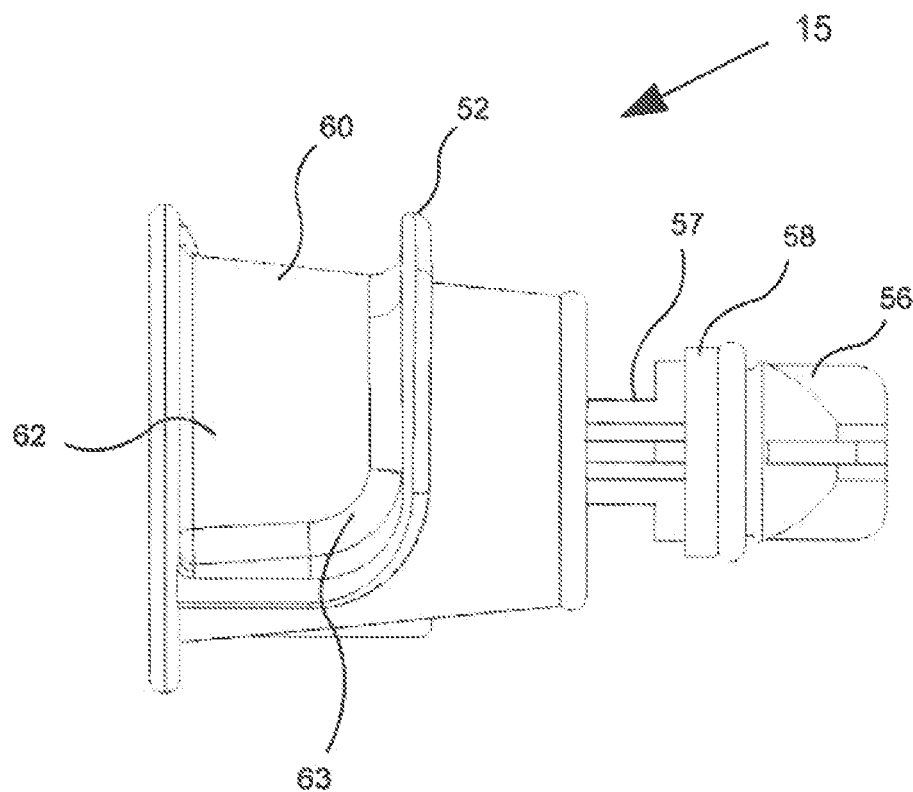
FIG. 10: is a bottom view of the one way of FIG. 8.

Referring next to FIGS. 3 to 5 and in particular to FIGS. 8 to 10, it can be seen that the inlet valve 15 includes a generally cylindrical or frusto-conical valve body 52 through which a plurality of apertures 53 extend from a first side 54 to an axially opposite side 55. A closure means 56 is provided which includes a stem 57 and a head 58. The stem 57 is slidably engaged with a guide aperture 58a provided in the valve body 52. The valve head 58 is biased against a sealing means 59, best seen in FIG. 4, by a suitable biasing means such a spring (not shown). In the embodiment shown the sealing means 59 is provided at the and of the barrel 11, although in other embodiments (not shown) the head 58 may seal against a sealing means which is connected to or integral with the valve body.

The closure means 56 allows liquid to flow through the apertures 53 from the inlet 4 to the barrel 11, but prevents flow in the opposite direction, as is common with one way valve mechanisms of the prior art.

A channel 60 is defined on an outer surface of the valve body 52, and extends from one side 61 of the body 15 to the radially opposite side 62. The channel 60 defines a flow path for the fluid when the plunger 12 is extended towards the valve 15. The flow path directs fluid from an area at or adjacent the top of the barrel 11 to the barrel outlet 18, which in the embodiment shown is provided in a lower surface of the barrel 11, best seen in FIGS. 3 to 5. Taking fluid from the top of the barrel 11 ensures that any entrained air in the barrel 11 is purged as efficiently as possible, as air bubbles in the fluid tend to rise to the top of the barrel 11.

In a preferred embodiment the channel 60 extends around one side of the valve body 52 only, in order to avoid any turbulence which might be caused if the fluid flowed around both sides of the body 52 and was recombined into a single stream. The channel 60 preferably has a cross-sectional area at least equal to that of the barrel outlet 18 in order to minimise the resistance to the fluid flowing through the channel 60, thereby minimising the force necessary to drive the plunger 11. The valve body 52 preferably fits snugly within the barrel 11, so that the flow path is defined by the cavity created between the channel 60 and the barrel 11, as best seen in FIG. 4.

As can be seen in FIGS. 8-10, the channel 60 is preferably provided with radiused corners 63. It is preferred that sharply angular changes in direction are avoided, as these can cause eddies in the fluid flow and/or areas of flow or no flow, which may trap entrained air bubbles in the fluid flow and make purging the applicator of air more difficult.

Referring next to FIG. 4, a conduit 64 extends between the barrel outlet 18 and the one way outlet valve 17 provided adjacent outlet nozzle 16. In a preferred embodiment the combined volume of the conduit 64 and the channel 60 is less than the volume of fluid dispensed by the dispensing means 100 her set to its lowest dose setting. If the conduit 64 has a greater volume than the minimum dose, then at low dose settings bubbles in the fluid may be carried only part of the way to the outlet valve 17 with a first dose of fluid, and may then float back up the conduit 64 before the next dose is expressed.

In some embodiments (not shown) the outlet valve 17 may be positioned on top of the barrel 11, thereby eliminating the need for the integrated net valve/outlet channel. Alternatively the outlet valve could be positioned immediately under the integrated inlet valve/outlet channel. However, both these options cause the end of the barrel to became quite bulky.

An additional advantage to having the outlet valve 17 close to the nozzle 16 is that the weight of fluid in the conduit 64 is held by the outlet valve 17, eliminating the need for a non-drip valve at the nozzle 16 for most applications.

In some embodiments a spherical valve element may be used instead of the head 56 and stem 57 shown in FIGS. 8 to 10. Such a ball-valve arrangement is well know to those skilled in the art, and may include the use a rubberised ball sealing against the end of the barrel, a hard bail with a soft seat, or a high precision hard ball/hard seat configuration.

Although the flow path from barrel 11 to the nozzle outlet 21 is shown as running inside the elongate handle 10, in less preferred embodiment (not shown) the nozzle inlet 20 may connect directly to the barrel 11, but may be shaped so that the nozzle outlet 21 exits at the opposite end of the elongate handle to the barrel 11 in substantially the same position as the nozzle outlet shown in FIGS. 2-5.

Figure 11:
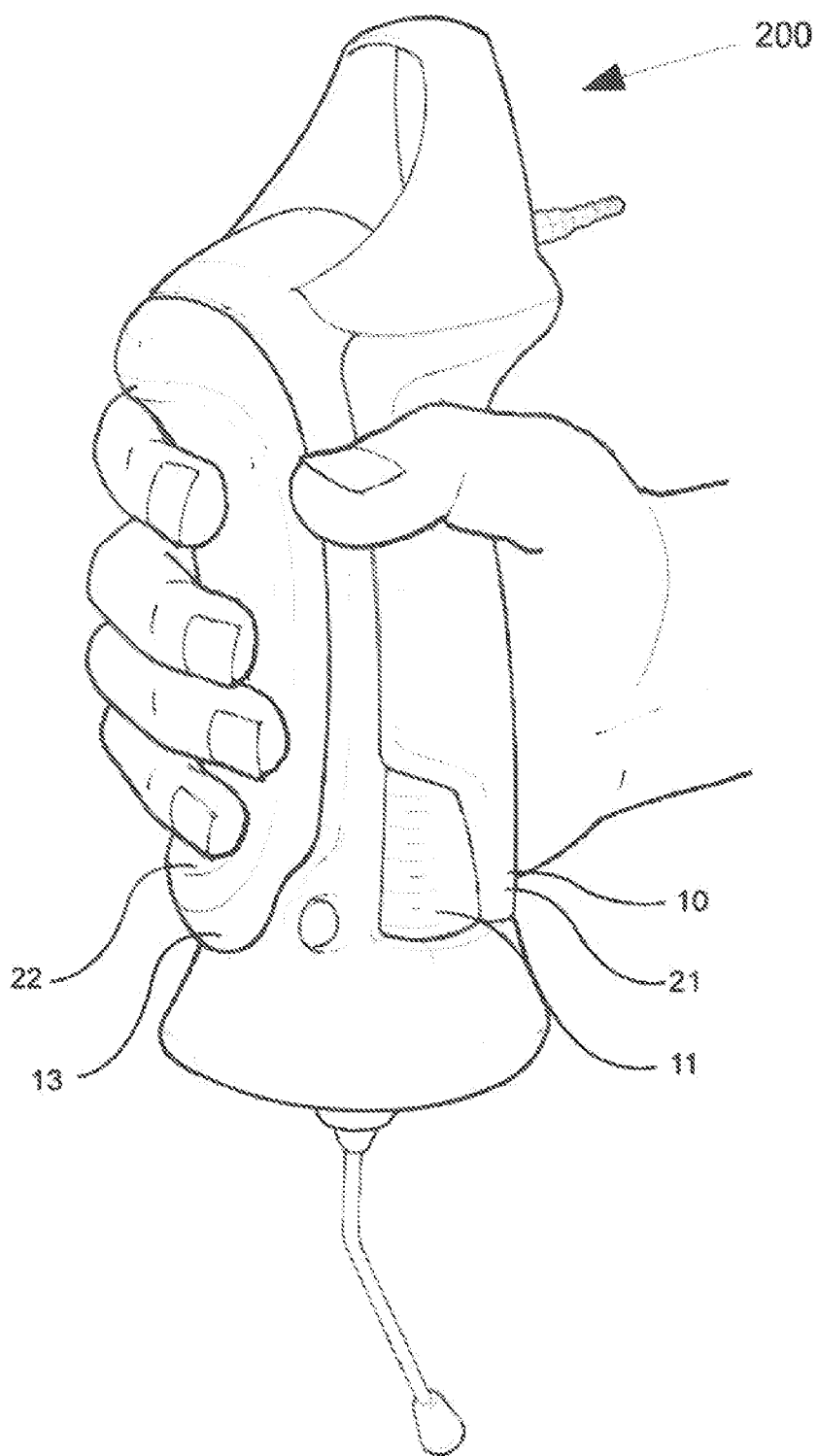
FIG. 11 Is a side perspective view of a second preferred embodiment of the dispensing means of the present invention with a flow control member in a dispensing position.

Referring next to FIGS. 11, 12 and 13, an alternative embodiment of the dispensing means is generally referenced 200. In this embodiment the dispensing means 200 has first an elongate handle means 10, and a second handle means 13 hingeably mounted to the elongate handle means 10 in a similar configuration to the embodiment shown in FIGS. 2 to 10. However, in this embodiment the barrel 11 is provided inside the first handle means 13.

The second handle means 13 is provided with a toothed rack 64 which engages gear or pinion 65, such that squeezing the second handle 13 towards the first handle 10 causes the rack 64 to rotate the gear 65. A plunger 66 is connected to a toothed push rod 67 which is preferably engaged directly with the gear 65, although in an alternative embodiment (not shown) the push rod 67 may be engaged with a second gear which rotates with the gear 65. The push rod 67 may be integrally formed with the plunger 66.

The preparation enters the barrel 11 from as inlet 58 through a flow path 69 in the push rod 67 via a one way inlet valve 70 which is integral with the plunger 66. A one way outlet valve 1 is provided at the barrel outlet.

As with the embodiment shown in FIGS. 2-5, a nozzle 16 has an inlet 20 in fluid communication with the outlet valve 17 and an outlet aperture 21. The central axis of the outlet aperture 21 and the longitudinal axis A of the elongate handle 10 form an angle of between 0° and 45°, so that the angle between the nozzle and the forearm of the user is between 30° and 90° when the user has his or her wrist in a relaxed position. The outlet valve 17 is also provided at the opposite end of the elongate handle means 10 to the inlet 68.

Although the embodiment shown in FIGS. 11-13 may function well, the embodiment shown in FIGS. 2-7 may be preferred because the arrangement of the barrel 11 with its central axis C at an angle of between 60° and 90°, or more preferably between 70° and 90°, to the longitudinal axis A of the elongate handle 10 allows a more direct actuation of the plunger 12 by the second handle 13, without the need for a rack and gear arrangement. This may lead to improved reliability of the applicator, and to an improved "feel" as to whether the correct dose has been applied, in a preferred embodiment the central axis C of the barrel 11 forms an angle of substantially 90° to the longitudinal axis A of the elongate handle 10.

The feel, and the accuracy and repeatability of the dosage dispensed, may also be improved if the barrel 11 has a greater length dimension than its diameter. In a preferred embodiment the length to diameter ratio of the barrel is between 2:1 and 2.6:1.

Figure 14:
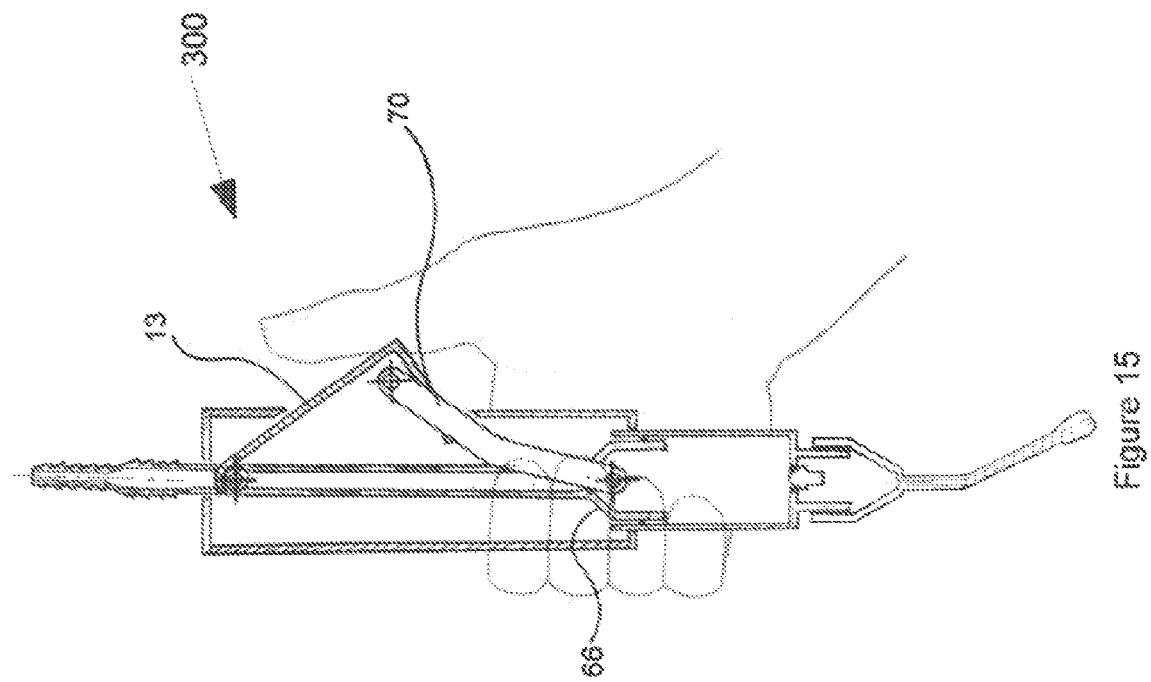
FIG. 14 Is a cross-section side view of a third embodiment of dispensing means, held in a position to allow the flow control member to be operated by the user's fingers.
Figure 15:
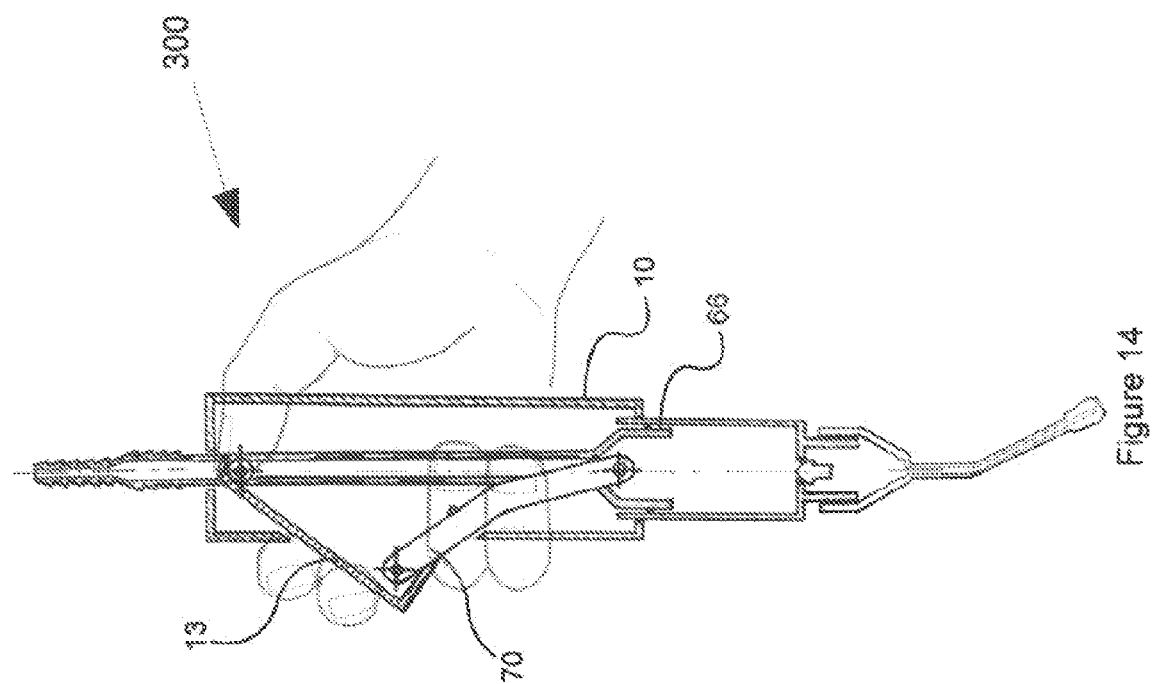
FIG. 15 Is a cross-section side view of the embodiment shown in FIG. 14, held in a position to allow the flow control member to be operated by the user's thumb.

FIGS. 14 and 15 show third possible embodiment of the dispensing means, generally referenced 300. This embodiment of the dispensing means differs from that shown in FIGS. 11-13 in that the plunger 66 is actuated by a connecting rod 70 which is rotatably connected to the second handle 13 at a first end and rotatably connected to the plunger 66 at a second end.

The dispensing means 300 can be held so that the second handle 13 is actuated with the fingers, as shown in FIG. 14, or with the thumb, as shown in FIG. 15.

While the examples of the dispensing means of the present invention described above are configured as oral drenchers, alternative embodiments of the dispensing means may be configured for use with alternative methods of dispensing an animal remedy such as pour-on, nasal infusion or injection.

Similarly, while the dispensing means shown is a manually actuated type, alternative embodiments of the invention may be powered electrically or by pressurised gas, or the remedy may be delivered to the dispensing means under pressure and the dispensing means may control the flow of the remedy by opening and closing a valve between the inlet and the nozzle outlet.

Those skilled in the art appreciate that dispensing means made in accordance with the present invention may be more comfortable to use than the dispensing means of the prior art, and may be less fatiguing to use over extended periods of time. Where the preparation dispensed is intended to be swallowed by the animal, the dispensing means of the present invention may allow the user to position the nozzle more accurately in the animal's mouth and may reduce the likelihood of injury to the animal during the application process.

Where in the foregoing description, reference has been made to specific components or integers of the invention having known equivalents, then such equivalents are herein incorporated as if individually set forth.

Although this invention has been described by way of example and with reference to possible embodiments thereof, it is to be understood that modifications or improvements may be made thereto without departing from the spirit or scope of the appended claims.

The invention claimed is:

1. An animal remedy dispenser for oral administration, comprising:
    an elongate handle means having a longitudinal axis;
    an inlet for receiving a remedy to be dispensed;
    an outlet aperture separate from the inlet for dispensing the remedy, the outlet aperture having a central axis; and
    flow control means for controlling flow of the remedy from the inlet to the outlet;
wherein the central axis of the outlet aperture and the longitudinal axis of the elongate handle means form an angle of between 0° and 45°;
wherein the flow control means includes a flow control member, and relative movement of the flow control member towards the elongate handle causes the remedy to flow from the outlet; and wherein the dispenser includes a barrel and a plunger reciprocable within the barrel upon relative movement of the elongate handle and the flow control member, the barrel provided with an inlet port in fluid communication with the inlet, and an outlet port in fluid communication with the outlet aperture, wherein a central axis of the barrel and the longitudinal axis of the elongate handle form an angle of between 70° and 90°.

2. The animal remedy dispenser of claim 1, wherein the central axis of the outlet aperture and the longitudinal axis of the elongate handle means form an angle of between 0° and 35°.

3. The animal remedy dispenser of claim 2, wherein the central axis of the outlet aperture is substantially parallel to the longitudinal as of the elongate handle means.

4. The animal remedy dispenser of claim 1, wherein the inlet is proximate a first end of the elongate handle means and the outlet aperture is proximate a second end of the handle means, opposite the first end.

5. The animal remedy dispenser of claim 1, wherein the distance between the center of the outlet aperture and the longitudinal axis of the elongate handle means is between 10 mm-35 m.

6. The animal remedy dispenser of claim 1, wherein the central axis of the barrel and the longitudinal axis of the first handle form an angle of substantially 90°.

7. An animal remedy dispenser according to claim 1, comprising in addition a dosage control mechanism including a dosage control part moveable between a first position wherein the dose dispensed by the dispenser can be adjusted, and a second position wherein the dose dispensed cannot be adjusted.

8. An animal remedy dispenser according to claim 7, wherein the dose is adjustable by rotation of the dosage control part about an axis of rotation, and movement of the dosage control part between the first position and the second position includes a movement parallel to the direction of the axis of rotation.

9. An animal remedy dispenser according to claim 7, wherein the dispenser includes a housing, and the dosage control part is rotatable within the housing, wherein one of the housing and the dosage control part is provided with at least one protruding member and the other is provided with a plurality of grooves or channels, adapted to receive at least one of the at least one protruding members when the dosage control part is in the second position.

10. An animal remedy dispenser according to claim 9, wherein the at least one protruding member includes a plurality of ribs.

11. An animal remedy dispenser according to claim 10, wherein the plurality of grooves or channels are defined by spaces between a plurality of second ribs.

12. An animal remedy dispenser according to claim 7, wherein activation of the dispensing means moves the dosage control part from the first position to the second position, if the dosage control part is not already in the second position when the dispensing means is activated.

13. An animal remedy dispenser according to claim 1, comprising in addition; a one way valve including a valve body having at least one aperture therethrough;
a closure means adapted to allow a fluid to flow through the at least one aperture in a first direction and to substantially prevent a fluid from flowing through the at least one aperture in a second direction opposite to the first direction;
wherein the valve body is provided with a flow path for receiving a fluid flowing in the second direction and directing the fluid to a required location.

14. An animal remedy dispenser according to claim 13, wherein the flow path of the one way valve extends around a periphery of the valve body.

15. An animal remedy dispenser according to claim 13, wherein the valve body includes a substantially cylindrical or frusto-conical portion and the flow path extends between radially opposite sides of the substantially cylindrical or frusto-conical portion.

16. An animal remedy dispenser according to claim 13, wherein the valve body is provided with a valve guide, and the closure means includes a valve head and a valve stem slidingly engaged with the valve guide.

17. An animal remedy dispenser according to claim 13, wherein the closure means includes a biasing means element for biasing the valve head towards a sealing means.

18. An animal remedy dispenser according to claim 13, wherein the flow path includes a channel.

19. An animal remedy dispenser according to claim 7, comprising in addition; a one way valve including a valve body having at least one aperture therethrough;
a closure means adapted to allow a fluid to flow through the at least one aperture in a first direction and to substantially prevent a fluid from flowing through the at least one aperture in a second direction opposite to the first direction;
wherein the valve body is provided with a flow path for receiving a fluid flowing in the second direction and directing the fluid to a required location.

20. An animal remedy dispenser according to claim 19, wherein the flow path of the one way valve extends around a periphery of the valve body.

21. An animal remedy dispenser according to claim 19, wherein the valve body includes a substantially cylindrical or frusto-conical portion and the flow path extends between radially opposite sides of the substantially cylindrical or frusto-conical portion.

22. An animal remedy dispenser according to claim 19, wherein the valve body is provided with a valve guide, and the closure means includes a valve head and a valve stem slidingly engaged with the valve guide.

23. An animal remedy dispensing moans dispenser according to claim 19, wherein the closure means includes biasing means for biasing the valve head towards a sealing means.

24. An animal remedy dispenser according to claim 19, wherein the flow path includes a channel.

* * * * *